United States Patent [19]

Branca et al.

[11] Patent Number: 4,472,435
[45] Date of Patent: Sep. 18, 1984

[54] BENZOPHENONE DERIVATIVES USEFUL IN TREATING HEART FAILURE

[75] Inventors: Quirico Branca, Basel; Albert E. Fischli; André Szente, both of Riehen, all of Switzerland

[73] Assignee: Hoffmann-LaRoche Inc., Nutley, N.J.

[21] Appl. No.: 283,579

[22] Filed: Jul. 15, 1981

[30] Foreign Application Priority Data

Jul. 31, 1980 [CH] Switzerland .................. 5840/80

[51] Int. Cl.³ ............... C07C 131/00; C07C 103/44; A61K 31/165
[52] U.S. Cl. .................................. 424/324; 424/327; 564/195; 564/220; 564/256; 564/266
[58] Field of Search ............. 564/220, 256, 266, 195; 424/324, 327

[56] References Cited

U.S. PATENT DOCUMENTS

| | | | |
|---|---|---|---|
| 3,121,074 | 2/1964 | Keller et al. | 564/220 X |
| 3,202,699 | 8/1965 | Stempel | 564/195 X |
| 3,465,038 | 9/1969 | Dolan | 564/266 |
| 3,513,191 | 5/1970 | Bell | 564/220 X |
| 3,887,604 | 6/1975 | Archer et al. | 564/220 X |
| 4,022,832 | 5/1977 | Tachikawa et al. | 564/195 |

FOREIGN PATENT DOCUMENTS

| | | | |
|---|---|---|---|
| 471999 | 1/1974 | Australia | 564/195 |
| 332 | 1/1979 | European Pat. Off. . | |
| 1618518 | 3/1971 | Fed. Rep. of Germany . | |
| 2327715 | 12/1973 | Fed. Rep. of Germany . | |
| 154228 | 12/1975 | Japan | 564/195 |
| 1144516 | 3/1969 | United Kingdom . | |

Primary Examiner—Thomas A. Waltz
Attorney, Agent, or Firm—Jon S. Saxe; Bernard S. Leon; Frank P. Hoffman

[57] ABSTRACT

There is presented novel benzophenone derivatives of the formula

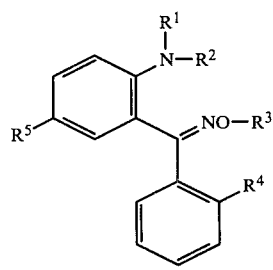

I wherein $R^1$ is hydrogen or lower alkyl, $R^2$ is hydrogen or aminoacetyl, $R^3$ is hydrogen or lower alkyl, $R^4$ is hydrogen or halogen, $R^5$ is hydrogen, amino, nitro or a group of the formula $R^3-ON=C(R^6)-$ and $R^6$ is lower alkyl, with the proviso that $R^5$ is a group of the formula $H-ON=C(R^6)-$ when $R^2$ and $R^3$ are both hydrogen, and their pharmaceutically acceptable acid addition salts.

The compounds exhibit aldosterone-antagonistic properties and are accordingly suitable for the control or prevention of heart failure, hepatic ascites, primary aldosteronism and idiopathic hypertension.

6 Claims, No Drawings

BENZOPHENONE DERIVATIVES USEFUL IN TREATING HEART FAILURE

DESCRIPTION OF THE INVENTION

The present invention is concerned with novel benzophenone oxime derivatives of the formula

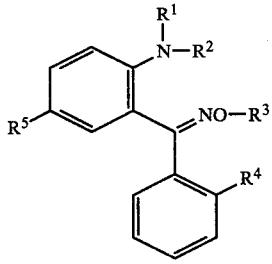

I and pharmaceutically acceptable acid addition salts of compounds of formula I.

The term "lower alkyl" denotes straight-chain or branched-chain saturated hydrocarbon groups containing at most 7, preferably at most 4, carbon atoms such as methyl, ethyl, n-propyl, isopropyl, n-butyl, t-butyl etc. The term "halogen" signifies fluorine, chlorine, bromine or iodine.

Among the compounds of formula I there are preferred those in which $R^1$ is hydrogen or methyl. $R^2$ preferably is aminoacetyl. $R^3$ preferably is hydrogen or methyl. $R^4$ preferably is hydrogen, fluorine or chlorine.

An especially preferred compound in the scope of the present invention is 2-amino-2'-[o-fluoro-α-(hydroxyimino)benzyl]-4'-[1-(hydroxyimino)ethyl]acetanilide.

Further compounds of formula I which are preferred in the scope of the present invention are:

2-Amino-2'-[o-chloro-α-(hydroxyimino)benzyl]-4'-nitro-acetanilide;
2-amino-2'-[α-(hydroxyimino)benzyl]-4'-nitro-acetanilide;
2,4'-diamino-2'-[o-chloro-α-(hydroxyimino)benzyl]-N-methyl-acetanilide;
2-amino-2'-[o-fluoro-α-(hydroxyimino)benzyl]-4'-nitro-acetanilide;
2-amino-2'-fluoro-5-[1-(hydroxyimino)ethyl]benzophenone oxime and
2-amino-benzophenone O-methyl oxime.

The novel benzophenone oxime derivative of formula I and their pharmaceutically acceptable acid addition salts can be manufactured in accordance with the invention by (a) reacting a benzodiazepine derivative of the formula

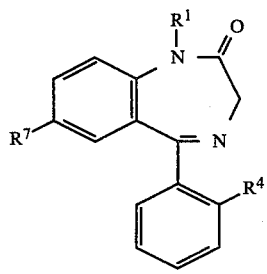

II wherein $R^7$ is hydrogen, amino, nitro or a group of the formula $R^3$—ON═C($R^6$)— or O═C($R^6$)— and $R^1, R^3, R^4$ and $R^6$ are as above with a compound of the formula $$R^3-ONH_2 \quad \text{III}$$

wherein $R^3$ is as above, or (b) hydrolyzing a compound of the formula

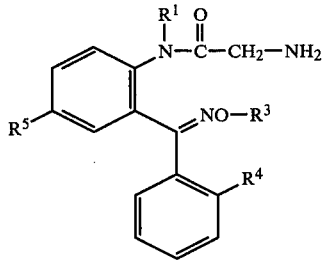

Ia wherein $R^1, R^3, R^4$ and $R^5$ are as above, with the proviso that $R^5$ is a group of the formula H—ON═C($R^6$)—, in which $R^6$ is as above, when $R^3$ is hydrogen, or (c) alkylating a compound of the formula

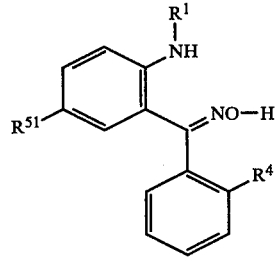

Ib wherein $R^{51}$ is hydrogen, amino, nitro or a group of the formula H—ON═C($R^6$)— and $R^1, R^4$ and $R^6$ are as above, at the oxime oxygen atom(s), or (d) reacting a benzophenone derivative of the formula

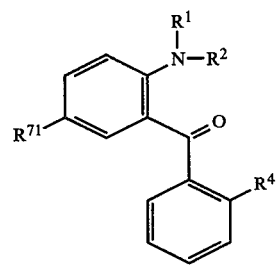

IV wherein $R^{71}$ is hydrogen, amino, nitro or a group of the formula O═C($R^6$)— and $R^1, R^2, R^4$ and $R^6$ are as above, with a compound of the formula $$R^3-ONH_2 \quad \text{III}$$

wherein $R^3$ is as above, or (e) converting a benzophenone oxime derivative of formula I into a pharmaceutically acceptable acid addition salt.

In accordance with embodiment (a) of the process, the novel benzophenone oxime derivatives of formula I can be manufactured by reacting benzodiazepine derivatives of formula II with hydroxylamine derivatives of formula III, preferably with acid addition salts thereof. This reaction is conveniently carried out in a basic solvent which is inert under the reaction conditions, for example in tertiary amines such as pyridine, triethylamine and the like. The reaction can, however, also be carried out in an alcohol such as, for example, methanol, ethanol and the like or in mixtures thereof with water and in the presence of an acid-binding agent such as, for example, potassium carbonate, sodium carbonate and the like. The temperature is not critical and the reaction can therefore be carried out at a temperature from about room temperature to the boiling point of the reaction mixture, the latter being preferred.

In accordance with embodiment (b) of the process, benzophenone oxime derivatives of formula I can be manufactured by hydrolyzing compounds of formula Ia. The conditions which are necessary for this hydrolysis can readily be ascertained by any person skilled in the art. Conveniently, the hydrolysis is carried out using aqueous sodium hydroxide or potassium hydroxide at a temperature from about room temperature to about 100°, preferably at about 50°.

In accordance with embodiment (c) of the process, benzophenone oxime derivatives of formula I can be manufactured by alkylating compounds of formula Ib at the oxime oxygen atom(s). This alkylation can be carried out using any suitable alkylating agent; for example, a corresponding halide such as methyl iodide or ethyl iodide or a dialkyl sulphate such as dimethyl sulphate. The alkylation is conveniently carried out in an inert organic solvent, for example in an ether such as tetrahydrofuran, dioxan or dimethoxyethane, or in another aprotic dipolar solvent, in the presence of an acid-binding agent such as, for example, sodium hydroxide or potassium hydroxide or the like. A small amount of a quaternary ammonium salt such as, for example, tetra-n-butyl-ammonium bromide, is preferably used as the catalyst. The alkylation is conveniently carried out at about room temperature, but it can also be carried out at a temperature above room temperature.

In accordance with embodiment (d) of the process, benzophenone oxime derivatives of formula I can be manufactured by reacting compounds of formula IV with hydroxylamine derivatives of formula III. The conditions which are necessary for this reaction can readily be ascertained by any person skilled in the art. For example, the reaction can be carried out in analogy to embodiment (a) of the process (i.e. in analogy to the reaction of compounds of formula II with compounds of formula (III).

In accordance with embodiment (e) of the process, benzophenone oxime derivatives of formula I can be converted into pharmaceutically acceptable acid addition salts. The manufacture of such salts is carried out according to generally customary methods. There come into consideration not only salts with inorganic acids but also salts with organic acids; for example, hydrochlorides, hydrobromides, sulphates, citrates, acetates, succinates, methanesulphonates, p-toluenesulphonates and the like.

The compounds of formula II and IV which are used as starting materials belong to classes of substances which are known per se. Representatives which have not specifically been previously described can be prepared according to methods which are known and familiar to any person skilled in the art. For example, compounds of formula II in which $R^7$ signifies a group of the formula $R^3-O-N=C(R^6)-$ can be prepared from the corresponding compounds of formula II in which $R^7$ signifies a group of the formula $R^6-CO-$ by treatment with a compound of formula III under mild conditions; for example, by reacting a compound of formula II in which $R^7$ is a group of the formula $R^6-CO-$ with hdroxylamine hydrochloride in pyridine or a mixture thereof with ethanol at room temperature.

Surprisingly, it has been shown that the novel benzophenone oxime derivatives of formula I hereinbefore exhibit pronounced aldosterone-antagonistic properties. These aldosterone-antagonistic properties can be dmonstrated in adrenalectomized rats as illustrated hereinafter.

If aldosterone is administered to adrenalectomised rats, then there is observed, in comparison to untreated animals, a pronounced reduction of the sodium excretion (sodium retention), an increased potassium excretion (potassium excretion) as well as a reduction of the excreted urine volume. If compounds of formula I are administered to the animals before the treatment with aldosterone, then there is observed, in comparison with the animals which are treated only with aldosterone (control animals), a pronounced increase of the sodium excretion (i.e. the sodium retention caused by aldosterone is antagonised), whereas the potassium excretion and the urine volume are influenced to a lesser extent.

The standard experiment is carried out as follows:

Female Holtzmann rats (150-180 g) are bilaterally adrenalectomised 70 to 74 hours before the beginning of the experiment. After the operation, the animals receive a customary rat dry feed and 0.9% sodium chloride solution for drinking. 16-17 hours before the beginning of the experiment the feed is removed from the animals, but they can subsequently drink, as before, 0.9% sodium chloride solution ad libitum. At the beginning of the experiment the substance to be tested as an aldosterone-antagonist is administered to the animals by means of a stomach probe. 30 minutes later the animals receive a subcutaneous injection of 4 mmg/kg of aldosterone. After a further 90 minutes, the urinary bladders of the animals are emptied by careful suprapubic pressure, whereupon the animals are placed individually in metabolic cages without food and without drink. The urine of the animals is then collected for 3 hours, whereupon their urinary bladders are once more emptied. The spontaneously excreted urine and the remaining urine obtained at the conclusion of the experiment by pressing-out the urinary bladders are collected in graduated centrifuge glasses. Sodium and potassium concentrations in the urine are determined with a flame photometer.

The following Table contains results obtained in the previously described experiment with representative compounds of general formula I. In this Table there are given for each of the compounds figuring therein the dosage administered (in mg/kg p.o.) as well as the percentage variation in the urine volume, the sodium excretion and the potassium excretion in comparison with the control animals (i.e. in comparison with the animals treated only with aldosterone). Moreover, the Table contains data concerning the acute toxicity of the compounds investigated (LD 50 in mg/kg in the case of single oral administration to mice).

TABLE

| | | | | | Toxicity and activity in adrenalectomised rats | | | | |
|---|---|---|---|---|---|---|---|---|---|
| $R^1$ | $R^2$ | $R^3$ | $R^4$ | $R^5$ | Dosage mg/kg p.o. | Volume in %, based | $[Na^+]$ on control | $[K^+]$ animals | LD 50 mg/kg p.o. |
| H | —COCH$_2$NH$_2$ | OH | Cl | —NO$_2$ | 0.1 | 114 | 211 | 99 | >5000 |
| H | —COCH$_2$NH$_2$ | OH | H | —NO$_2$ | 0.1 | 152 | 230 | 97 | >5000 |
| CH$_3$ | —COCH$_2$NH$_2$ | OH | Cl | NH$_2$ | 1 | 155 | 254 | 94 | >5000 |
| H | —COCH$_2$NH$_2$ | OH | F | $\underset{CH_3-C=N-OH}{\mid}$ | 1 | 156 | 327 | 102 | >5000 |
| | | | | | 0.01 | 161 | 215 | 86 | |

The benzophenone oxime derivatives of formula I and their pharmaceutically acceptable acid addition salts can be used as medicaments, for example in the form of pharmaceutical preparations. The pharmaceutical preparations can be administered orally, for example in the form of tablets, coated tablets, dragées, hard and soft gelatin capsules, solutions, emulsions or suspensions. The administration can, however, also be carried out rectally (e.g. in the form of suppositories) or parenterally (e.g. in the form of injection solutions).

For the manufacture of tablets, coated tablets, dragees and hard gelatin capsules, the benzophenone oxime derivatives of formula I and their pharmaceutically acceptable acid addition salts can be processed with pharmaceutical inert, inorganic or organic excipients. Examples of such excipients which can be used for tablets, dragees and hard gelatin capsules are lactose, maize starch or derivatives thereof, talc, stearic acid or its salts etc.

Suitable excipients for soft gelatin capsules are, for example, vegetable oils, waxes, fats, semi-solid and liquid polyols etc. Depending on the nature of the active substance no excipients are, however, generally required in the case of soft gelatin capsules.

Suitable excipients for the manufacture of solutions and syrups are, for example, water, polyols, saccharose, invert sugar, glucose and the like.

Suitable excipients for injection solutions are, for example, water, alcohols, polyols, glycerine, vegetable oils etc.

Suitable excipients for suppositories are, for example, natural or hardened oils, waxes, fats, semi-liquid or liquid polyols and the like.

Moreover, the pharmaceutical preparations can contain preserving agents, solubilising agents, stabilising agents, wetting agents, emulsifying agents, sweetening agents, colouring agents, flavouring agents, salts for varying the osmotic pressure, buffers, coating agents or antioxidants. They can also contain still other therapeutically valuable substances.

As mentioned earlier, medicaments containing one or more compounds of formula I or pharmaceutically acceptable acid addition salts thereof are also an object of the present invention as is a process for the manufacture of such medicaments which is characterized by bringing one or more compounds of formula I or pharmaceutically acceptable acid addition salts thereof and, if desired, one or more other therapeutically valuable substances into a galenical administration form. A further object of the present invention is, as mentioned earlier, the use of benzophenone oxime derivatives of formula I and of pharmaceutically acceptable acid addition salts thereof in the control or prevention of illnesses, especially in the control or prevention of heart failure, of hepatic ascites, of primary aldosteronism and of idiopathic hypertension. The dosage can vary within wide limits and is, of course, adjusted to the individual requirements in any particular case. In general, in the case of oral administration a daily dosage of about 20 mg to 1500 mg should be appropriate.

In the following Examples which illustrate the present invention in more detail but are not intended to limit its extent, all temperature are given in degrees Centigrade.

EXAMPLE 1

A solution of 50 g (0.167 mol) of 5-(2-fluorophenyl)-1,3-dihydro-7-nitro-2H-1,4-benzodiazepin-2-one and 17.4 g (0.25 mol) of hydroxylamine hydrochloride in 200 ml of pyridine is heated to reflux overnight under argon. The mixture is concentrated in a rotary evaporator and the residue is taken up in methylene chloride. The organic phase is washed with water, dried and evaporated. The aqueous phase is extracted with chloroform overnight in a perforator. After drying and removing the solvent, the residue is combined with the crude product obtained above, suspended in 200 ml of methylene chloride and filtered off. There is obtained 2-amino-2'-[o-fluoro-α-(hydroxylimino)benzyl]-4'-nitro-acetanilide of melting point 198°.

EXAMPLE 2

A solution of 10 g (35.55 mmol) of 1,3-dihydro-7-nitro-5-phenyl-2H-1,4-benzodiazepin-2-one and 3.7 g (53.3 mmol) of hydroxylamine hydrochloride in 80 ml of pyridine is heated under reflux for 1 hour. After cooling, the mixture is taken up in methylene chloride, washed with water, dried and evaporated. The residual pyridine is removed in vacuo azeotropically with toluene. The solid crude product is suspended in hot tert.-butyl methyl ether and filtered off. There is obtained 2-amino-2'-[α-(hydroxyimino)-benzyl]-4'-nitro-acetanilide of melting point 167° (decomposition).

EXAMPLE 3

From 10 g (31.7 mmol) of 5-(o-chlorophenyl)-1,3-dihydro-7-nitro-2H-1,4-benzodiazepin-2-one there is obtained in analogy to the procedure described in Example 2 2-amino-2'-[o-chloro-α-(hydroxyimino)-benzyl]-4'-nitro-acetanilide of melting point 177° (decomposition).

EXAMPLE 4

Hydrogen chloride is introduced for 10 minutes into a solution of 5.25 g (15.05 mmol) of 2-amino-2'-[o-chloro-α-(hydroxyimino)-benzyl]-4'-nitro-acetanilide in 300 ml of methylene chloride and 100 ml of ethanol. The solution is evaporated to dryness in vacuo and the residue is dried overnight in vacuo. There is obtained 2-amino-2'-[o-chloro-α-(hydroxyimino)benzyl]-4'-nitro-acetanilide hydrochloride of melting point 140° (decomposition).

EXAMPLE 5

Hydrogen chloride is conducted for 10 minutes into a solution of 2.7 g (8.59 mmol) of 2-amino-2'-[α-(hydroxyimino)benzyl]-4'-nitro-acetanilide in 150 ml of methylene chloride and 30 ml of ethanol. The solution is subsequently evaporated to dryness and the residue is dried at 60° overnight in vacuo. There is obtained 2-amino-2'-[α-(hydroxyimino)benzyl]-4'-nitro-acetanilide hydrochloride of melting point 150° (decomposition).

EXAMPLE 6

A solution of 50 g (0.168 mol) of 7-acetyl-5-(o-fluorophenyl)-1,3-dihydro-2H-1,4-benzodiazepin-2-one and 50 g (0.719 mol) of hydroxylamine hydrochloride in 400 ml of pyridine is stirred at room temperature for 21 hours, concentrated in vacuo and the residual pyridine is removed azeotropically by repeated evaporation with toluene. 300 ml of water are added to the residue and the pH of the solution is adjusted to ca 7. The precipitate which thereby results is filtered off, washed with water and dried at 60° in vacuo over phosphorus pentoxide. There is obtained 2-amino-2'-[o-fluoro-α-(hydroxyimino)benzyl]-4'-[1-(hydroxyimino)ethyl]acetanilide hydrochloride of melting point 219°–220°.

EXAMPLE 7

10 g (26.26 mmol) of 2-amino-2'-[o-fluoro-α-(hydroxyimino)benzyl]-4'-[1-(hydroxyimino)ethyl]-acetanilide are treated with 3N sodium hydroxide at 50° for 1 hour. The pH of the solution is adjusted to 8 and the precipitated material is filtered off, washed with water and dried at 50° in vacuo over phosphorus pentoxide. There is obtained 2-amino-2'-fluoro-5-[1-(hydroxyimino)ethyl]benzophenone oxime as a foam of melting point ca 165°.

EXAMPLE 8

(a) 42.4 g of potassium carbonate and 18.5 ml of methyl iodide are added to a solution of 50 g (0.158 mol) of 5-(o-chlorophenyl)-1,3-dihydro-7-nitro-2H-1,4-benzodiazepin-2-one in 600 ml of acetone and the mixture is stirred at room temperature for 16 hours. After filtering-off insoluble material, the filtrate is evaporated and the residue is taken up in methylene chloride. The organic phase is washed once with water, dried and evaporated, there being obtained 5-(o-chlorophenyl)-1,3-dihydro-1-methyl-7-nitro-2H-1,4-benzodiazepin-2-one of melting point 220°.

(b) A total of 103 g of tin chloride dihydrate is added portionwise while stirring to a solution, cooled in ice, of 50 g (0.152 mol) of 5-(o-chlorophenyl)-1,3-dihydro-1-methyl-7-nitro-2H-1,4-benzodiazepin-2-one in 500 ml of concentrated hydrochloric acid so that the temperature remains below 85°. The mixture is stirred at room temperature for a further 3 hours, neutralised in the cold with 10N sodium hydroxide and the suspension is extracted in a perforator, firstly for 24 hours with 1.5 l of ethanol/chloroform (1:9) and then overnight with 1.5 l of ethanol/1,2-dichloroethane (1:4). After evaporating the extract, the residue is recrystallised from ethanol, 7-amino-5-(o-chlorophenyl)-1,3-dihydro-1-methyl-2H-1,4-benzodiazepin-2-one of melting point 238°–239° being obtained.

EXAMPLE 9

A solution of 5.0 g (16.68 mmol) of 7-amino-5-(o-chlorophenyl)-1,3-dihydro-1-methyl-2H-1,4-benzodiazepin-2-one and 1.74 g (22.02 mmol) of hydroxylamine hydrochloride in 50 ml of pyridine is heated to reflux for 2 hours under argon. After cooling, the mixture is taken up in 600 ml chloroform/ethanol (4:1) and washed with 250 ml of water. The aqueous phase is adjusted to pH 8, saturated with sodium chloride and extracted with chloroform overnight in a perforator. After drying and evaporating the solvent, the residue is suspended in hot tert.-butyl methyl ether and filtered off. There is obtained 2,4'-diamino-2'-[o-chloro-α-(hydroxyimino)benzyl]-N-methylacetanilide of melting point 150° (decomposition).

EXAMPLE 10

A solution of 3.0 g (14.15 mmol) of 2-amino-benzophenone oxime in 120 ml of tetrahydrofuran is treated successively with 1.07 g of potassium hydroxide, 100 mg of tetrabutylammonium bromide, 1.81 ml of dimethyl sulphate and the mixture is stirred at room temperature overnight. The mixture is taken up in methylene chloride, washed with water, dried and evaporated. The residue is twice suspended in boiling ether and filtered off, there being obtained 2-amino-benzophenone O-methyl oxime of melting point 138°.

EXAMPLE A

2-Amino-2'-[o-chloro-α-(hydroxyimino)benzyl]-4'-nitro-acetanilide can be used as follows as the active substance for the production of pharmaceutical preparations:

| (a) Tablets | 1 tablet contains |
|---|---|
| Active substance | 200 mg |
| Microcrystalline cellulose | 155 mg |
| Maize starch | 25 mg |
| Talc | 25 mg |
| Hydroxypropylmethylcellulose | 20 mg |
| | 425 mg |

The active substance is mixed with half of the microcrystalline cellulose and granulated with a 10 percent solution of hydroxypropylmethylcellulose in a mixture of isopropanol and methylene chloride. The granulate is dried, sieved and mixed with the rest of the adjuvants. Then, the mixture is pressed on a press to biplanar tablets having a diameter of 12 mm and a break-bar.

| (b) Capsules | 1 capsule contains |
|---|---|
| Active substance | 100.0 mg |
| Maize starch | 20.0 mg |
| Lactose | 95.0 mg |
| Talc | 4.5 mg |
| Magnesium stearate | 0.5 mg |
| | 220.0 mg |

The active substance is mixed with the adjuvants and sieved. After renewed mixing, the capsule fill mass obtained is filled into interlocking gelatin capsules of suitable size on a fully automatic capsule filling machine.

What is claimed:

1. A method to control or prevent heart failure, hepatic ascites, primary aldosterone or idiopathic hypertension in a patient in need of such treatment which comprises treating said patient with an aldosterone antagonistic amount of a compound of the formula

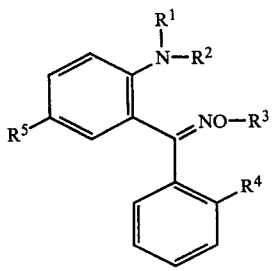

wherein R¹ is hydrogen or lower alkyl, R² is hydrogen or aminoacetyl, R³ is hydrogen or lower alkyl, R⁴ is hydrogen or halogen, R⁵ is hydrogen, amino, nitro or a group of the formula $R^3-ON=C(R^6)-$ and $R^6$ is lower alkyl, with the proviso that R⁵ is a group of the formula $H-ON=C(R^6)-$ when R² and R³ are both hydrogen, and pharmaceutically acceptable acid addition salts thereof.

2. The method of claim 1 wherein R¹ is hydrogen or methyl, R² is aminoacetyl, R³ is hydrogen or methyl and R⁴ is hydrogen, fluorine or chlorine.

3. The method of claim 2 wherein the compound is 2-Amino-2'-[o-fluoro-α-(hydroxyimino)benzyl]-4'-[1-hydroxyimino)ethyl]acetanilide.

4. The method of claim 1 wherein the compound is selected from the group consisting of 2-amino-2'[o-chloro-α-(hydroxyimino)benzyl]-4'-nitro-acetanilide, 2-amino-2'-[α-(hydroxyimino)benzyl]-4'-nitro-acetanilide, 2,4'-diamino-2-'[o-chloro-α-(hydroxyimino)benzyl]-N-methyl-acetanilide, 2-amino-2'-[o-(fluoro-α-(hydroxyimino)benzyl]-4'-nitro-acetanilide; 2-amino-2'-fluoro-5-[1-hydroxyimino)ethyl]-benzophenone oxime and 2-amino-benzophenone O-methyl oxime.

5. A composition for enteral or parenteral administration useful in the treatment of heart failure, hepatic ascites, primary aldosteronism and idiopathic hypertension which comprises an effective amount of a compound of the formula

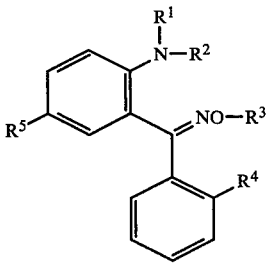

wherein R¹ is hydrogen or lower alkyl, R² is hydrogen or aminoacetyl, R³ is hydrogen or lower alkyl, R⁴ is hydrogen or halogen, R⁵ is hydrogen, amino, nitro or a group of the formula $R^3-ON=C(R^6)-$ and $R^6$ is lower alkyl, with the proviso that R⁵ is a group of the formula $H-ON=C(R^6)-$ when R² and R³ are both hydrogen, and pharmaceutically acceptable acid addition salts thereof together with a suitable pharmaceutical carrier.

6. The composition of claim 5 wherein the compound of formula I is 2-Amino-2'-[o-fluoro-α-(hydroxyimino)-benzyl]-4'-[1-hydroxyimino)ethyl]acetanilide.

* * * * *